United States Patent
Chou et al.

(10) Patent No.: US 8,333,876 B2
(45) Date of Patent: Dec. 18, 2012

(54) ION CONCENTRATION MEASUREMENT SYSTEM AND METHODS THEREOF

(75) Inventors: Jung-Chuan Chou, Yunlin County (TW); Chang-Chi Lee, Yunlin County (TW)

(73) Assignee: National Yunlin University of Science and Technology, Yunlin (TW)

( * ) Notice: Subject to any disclaimer, the term of this patent is extended or adjusted under 35 U.S.C. 154(b) by 476 days.

(21) Appl. No.: 12/631,764

(22) Filed: Dec. 4, 2009

(65) Prior Publication Data

US 2011/0056847 A1   Mar. 10, 2011

(30) Foreign Application Priority Data

Sep. 7, 2009  (TW) ................................ 98130038 A

(51) Int. Cl.
  *G01N 27/26* (2006.01)
(52) U.S. Cl. ........................................ 204/433; 204/415
(58) Field of Classification Search ............... 340/573.1, 340/572.1; 204/433, 415; 600/300, 424
See application file for complete search history.

(56) References Cited

U.S. PATENT DOCUMENTS

| | | | |
|---|---|---|---|
| 7,034,677 B2 * | 4/2006 | Steinthal et al. | 340/539.12 |
| 2005/0038332 A1 * | 2/2005 | Saidara et al. | 600/347 |
| 2008/0041721 A1 * | 2/2008 | Hsiung et al. | 204/415 |

OTHER PUBLICATIONS

D. Diamond, et al. 2.8 Application of ISEs, p. 52-53, in Principles of Chemical and Biological Sensors, John Wiley & Sons, Inc.: New York, 1998.*

* cited by examiner

*Primary Examiner* — J. Christopher Ball

(57) ABSTRACT

An ion concentration measurement system is provided. The ion concentration measurement system has: at least an end system having a sensing unit for measuring the ion concentration of a test solution to generate at least a sensing signal; a control unit for controlling the acquisition of the sensing signal; a display unit for displaying the sensing signal in real time; and an end wireless transmission interface for transmitting the sensing signal wirelessly.

22 Claims, 5 Drawing Sheets

ION CONCENTRATION MEASUREMENT SYSTEM AND METHODS THEREOF

CROSS REFERENCE TO RELATED APPLICATIONS

This Non-provisional application claims priority under 35 U.S.C. §119(a) on Patent Application No(s). 098130038, filed in Taiwan, Republic of China on Sep. 7, 2009, the entire contents of which are hereby incorporated by reference.

BACKGROUND OF THE INVENTION

1. Field of the Invention

The present invention relates to an ion concentration measurement system and method, and in particular relates to an ion concentration measurement system and method for displaying results in real time and transmitting the results wirelessly.

2. Description of the Related Art

Recently, sensors have been widely applied in different fields, such as the medical, biotechnological, food industry, agricultural, environmental monitoring and military affair, etc. The key devices for applicability, are readout circuits and signal processing for measurement system. The key conditions for applicability include real-time display, easy operation and portage, low cost, high accuracy and wireless capability, etc.

Microcontrollers have been widely used in industry. Microcontrollers usually comprise an operating unit, a control unit, a memory, and an input/output (I/O) port, among others. Microcontrollers are applied in different fields such as automation, electronics, artificial neural network (ANN) model, and sensor measurement system fields, etc. 8-bit, 16-bit, and 32-bit microcontrollers have been developed. The developmental languages of microcontrollers include assembly languages and high-level languages. The high-level languages provide faster operating speeds than the assembly languages.

The wireless sensing network was early developed by he U.S. Department of Defense supported academic community in 1980, but the cost was expensive for construction of wireless sensing network, so the wireless technique was stagnant. Recently, digitized home, medical management, sensor network, etc. are quickly developed, so the wireless technique is similarly applied in above fields.

BRIEF SUMMARY OF THE INVENTION

The present invention provides an ion concentration measurement system. The ion concentration measurement system comprises: at least an end system comprising a sensing unit for measuring the ion concentration of a test solution to generate at least a sensing signal; a control unit for controlling the acquisition of the sensing signal; a display unit for displaying the sensing signal in real time; and an end wireless transmission interface for transmitting the sensing signal wirelessly.

The present invention also provides an ion concentration measurement method. The ion concentration measurement method comprises: a measurement procedure and a transmission procedure. The measurement procedure comprises: measuring the ion concentration of a test solution to obtain a sensing signal; determining whether the sensing signal is stable; and storing the sensing signal when the sensing signal is determined as stable. The transmission procedure comprises transmitting the sensing signal to an electronic device wirelessly.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
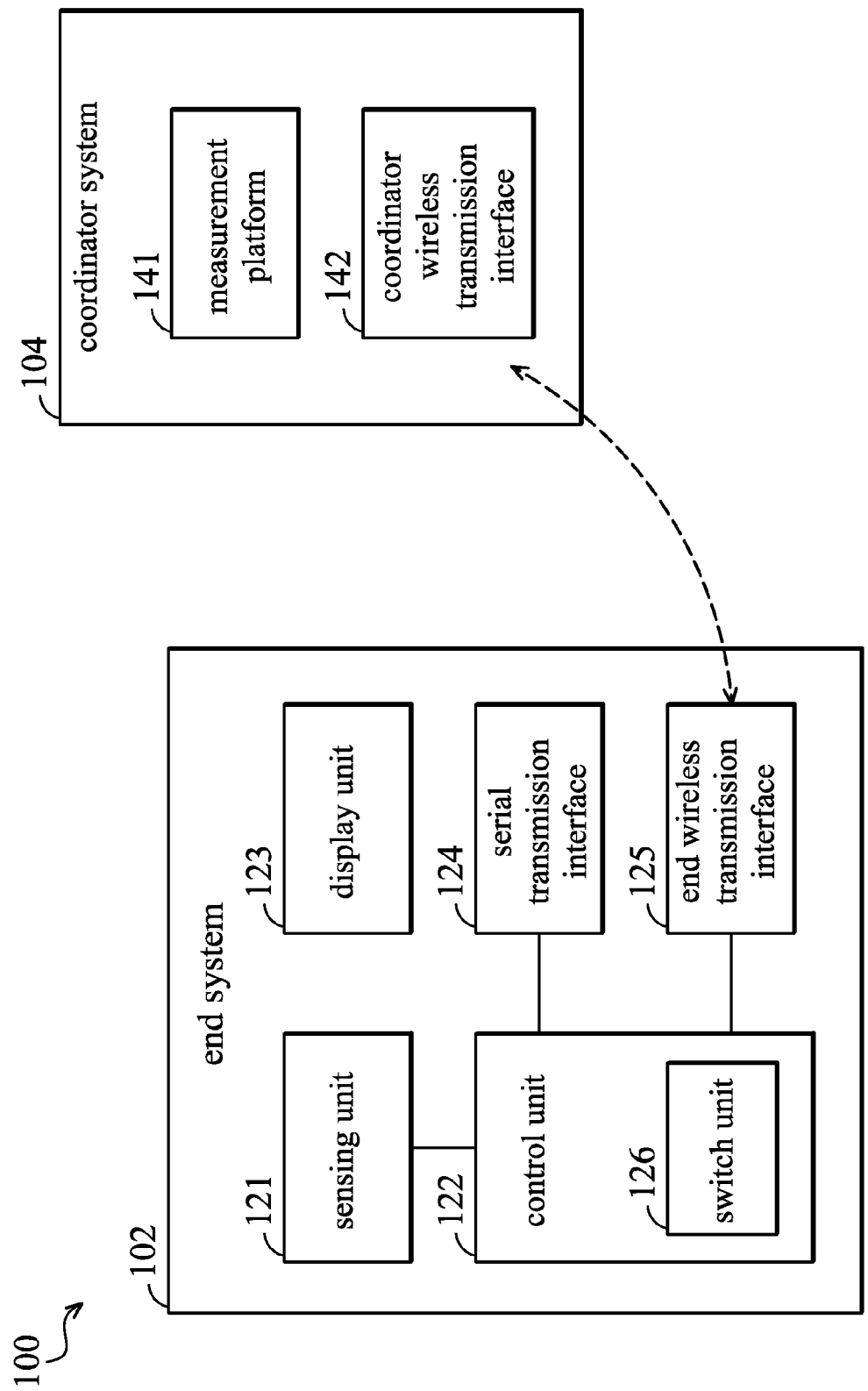
FIG. 1 illustrates an ion concentration measurement system in accordance with an exemplary embodiment of the present invention.

Referring to FIG. 1, FIG. 1 illustrates an ion concentration measurement system in accordance with an exemplary embodiment of the present invention. The ion concentration measurement system 100 comprises: at least an end system 102 and a coordinator system 104.

In a preferred embodiment, the end system 102 comprises a sensing unit 121, a control unit 122, a display unit 123, a serial transmission interface 124 and an end wireless transmission interface 125. In the present invention, the sensing unit 121 is used to measure the ion concentration (e.g. hydrogen ion concentration or chlorine ion concentration) from a test solution (not shown) and generate a plurality of sensing signals in respect to the ion concentration. Those skilled in the art will further appreciate that the number of the sensing unit 121 is not limited. The control unit 122 is used to control the acquisition of the sensing signals and calculate the pH values (acidity and basicity) of the test solution. The control unit 122, for example, comprises an analog to digital converter (not shown), a processor and a switch unit 126 for turning on or off the end system 102. In the present invention, if the display unit 123 (which is implemented as a LCD module or a matrix light emitting diode) displays the sensing signals in real time, the end system 102 of the ion concentration measurement system 100 having the display unit 123 may be a real time portable apparatus. Further, it is notable that the present invention comprises not only the serial transmission interface 124 for transmitting the sensing signals to a computer (not shown) coupled to the end system 102 but also the end wireless transmission interface 125 for wirelessly outputting the sensing signals to the other devices. The end wireless transmission interface 125 may use a ZigBee or MiWi protocol while the serial transmission interface 124 may use a RS-232 interface or an USB interface, but the present invention is not limited thereto.

In addition to the end system 102, the present invention further comprises a coordinator system 104 for coordinating the operation between the end system 102 and the coordinator system 104. In some embodiments, the coordinator system 104 is separated from the end system 102 and configured to further process the sensing signals as a data processing center among several end systems 102. For example, the coordinator system 104 may have a measurement platform 141 which is structured by LabVIEW software, wherein the measurement platform 141 may further readout, store, monitor, or display the sensing signal transmitted from the end system 102. In a preferred embodiment, the coordinator system 104 has a coordinator wireless transmission interface 142 for receiving the sensing signals from the end system 102 wirelessly.

The hardware arrangement of the ion concentration measurement system 100 in the present invention has been introduced above. The control unit 122 of the ion concentration measurement system 100 further has a special software design to implement an ion concentration measurement method according to the present invention. The ion concentration measurement method will be further described as follows.

Figure 2:
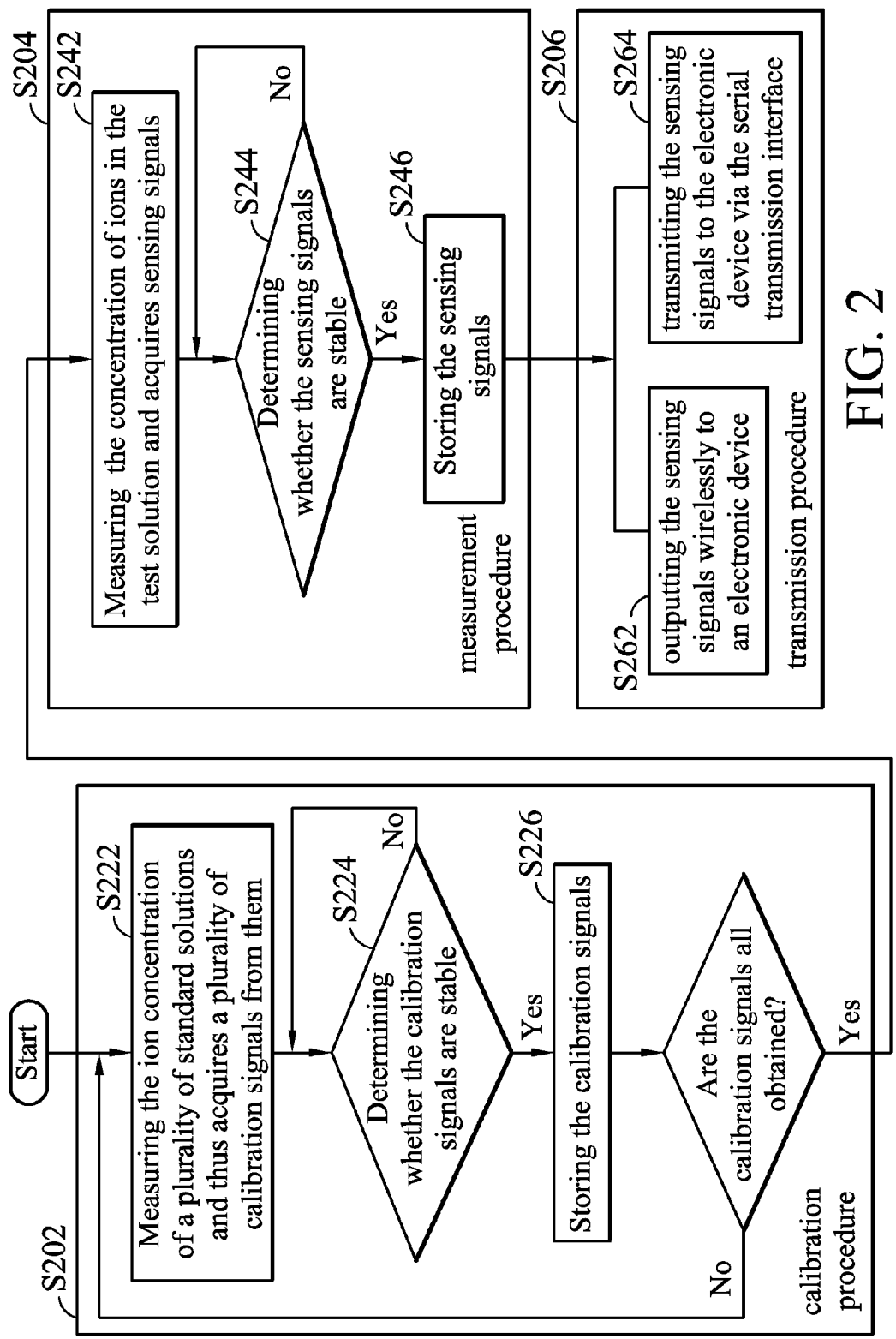
FIG. 2 shows the flow chart of the ion concentration measurement method according to the present invention.

Referring to FIG. 1 and FIG. 2, FIG. 2 shows the flow chart of the ion concentration measurement method according to the present invention. The method provided comprises a measurement procedure S204 and a transmission procedure S206. In some embodiments, the method of the present invention further comprises a calibration procedure S202. Following, the procedures mentioned above will be described together according to a preferred embodiment. The ion concentration measurement system 100 first starts, and then enters the calibration procedure S202. In the step S222, the sensing unit 121 measures the ion concentration of a plurality of standard solutions (for example, five standard solutions having concentration pH3, pH7, pH11, pCl and pCl4, respectively) and thus acquires a plurality of calibration signals from them. It is well known in the art, that the pH value is the concentration of hydrogen ion (also known as acidity and basicity) and defined by $pH=-\log_{10}[H^+]$; while the pCl value is the concentration of chlorine and defined by $pCl=-\log_{10}[Cl^+]$. In a preferred embodiment, the concentration of the standard solution is within pH1 and pH11. If the calibration procedure S202 is implemented by software, the software may further comprises a subroutine for determining whether the calibration signals are stable, as shown in step S224. Specifically, when the calibration signals are in the form of voltages, the step S224 is performed to determine whether the amounts that the voltages vary are smaller than a predetermined value. After the steps S222 and S224, when the calibration signals are determined as being stable, they will be stored, as shown in step S226. The ion concentration measurement method of the present invention then enters the measurement procedure S204. In step S242, the sensing unit 121 measures the concentration of ions (hydrogen ions or chlorine ions) in the test solution and acquires sensing signals. According to the present invention, similarly, the measurement procedure S244 may further comprise a step S244 for determining whether the sensing signals are stable. For example, when the sensing signals are in the form of voltages, the step S224 is performed to determine whether the amounts that the voltages vary are smaller than a predetermined value. After the step S242 and S244, when the sensing signals are determined as being stable, they will be stored, as shown in step S246. In the end, the ion concentration measurement method of the present invention enters the transmission procedure S206. The transmission procedure S206 includes a step S262 (mode #1) for outputting the sensing signals wirelessly to an electronic device and a step S264 (mode #2) for transmitting the sensing signals to the electronic device via the serial transmission interface 124. For example, the control unit 122 of the ion concentration measurement system 100 may determine and choose mode #1 or mode #2 for data transmission. The ion concentration measurement method of the present invention may be implemented by the end system 102 of FIG. 1 which was discussed above, and the electronic device to which the sensing signal is transmitted may be the coordinator system 104 separated from the end system 102 in FIG. 1 or a computer (not shown) which is coupled to the end system 102 via the serial transmission interface 124.

Figure 3:
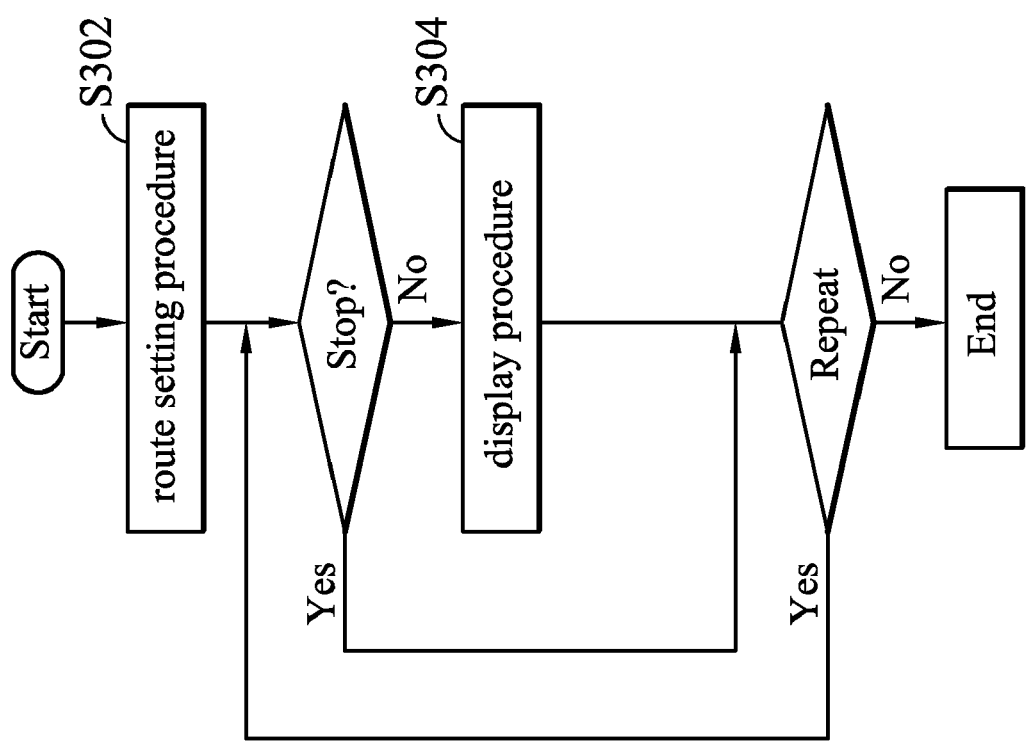
FIG. 3 is a flow chart of the route setting procedure and the display procedure.

The ion concentration measurement method of the present invention further comprises a route setting procedure and a display procedure. Referring to FIG. 1 and FIG. 3, FIG. 3 is a flow chart of the route setting procedure and the display procedure. The end system 102 of the ion concentration measurement system 100 may perform the route setting procedure 5302 such that a user, via the coordinator system 104 wirelessly connected to the end system 102 or via the computer connected to the end system 102, may set the route through which the sensing signals are stored and accessed. The end system 102 of the ion concentration measurement system 100 may perform the display procedure 5304 to display the sensing signals acquired from the measurement procedure on the display unit 123 in real time. In addition, when a user needs to know the sensing signals previously acquired, the user may access them through the previously set route.

An embodiment is provided here to explain the ion concentration measurement method of the present invention. Those skill in the art will appreciate that the present invention is not limited in this regard. The measurement procedure process in this invention is shown as following (pCl values are used for explanation):

(1) Switch ON, the sentence "Immerse in pCl0. ok?" is displayed on the screen of the display unit 123.

(2) The sensing unit 121 and reference electrode are connected with the end system 102.

(3) The sensing unit 121 and reference electrode are washed by deionized water, and then immersed in a pCl0 solution.

(4) Press switch, the sensing unit 121 starts to acquire the sensing signal.

(5) The sentence "Wait . . . " is displayed on the screen of the display unit 123, the process waits the calibration signals from the sensing unit 121 to become stable.

(6) The sentence "Immerse in pCl4. ok?" is displayed on the screen of the display unit 123.

(7) The sensing unit 121 and reference electrode are washed by deionized water, and then immerse in a pCl4 solution.

(8) Press switch, the sensing signal is obtained.

(9) The sentence "Wait . . . " is displayed on the screen of the display unit 123, the process waits the sensing signals from the sensing unit 121 to become stable.

(10) The sensing signals respectively corresponding to the standard solutions (here, pCl0 and pCl4 for example) are all obtained, furthermore, the "Immerse in test solution" is displayed on the screen of the display unit 123.

(11) The sensing unit 121 and reference electrode are washed by deionized water, and then immersed in a test solution.

(12) Press switch, the sensing signal is obtained.

(13) The "Wait . . . " is displayed on the screen of the display unit 123.

(14) After the sensing signals are stable, the sensing signals are transformed into pCl values.

(15) The pCl values are displayed on the screen of the display unit 123, and sent to the coordinator system 104 via the end wireless transmission interface 125.

(16) The processes from step (11)-(15) are repeated.

Figure 4:
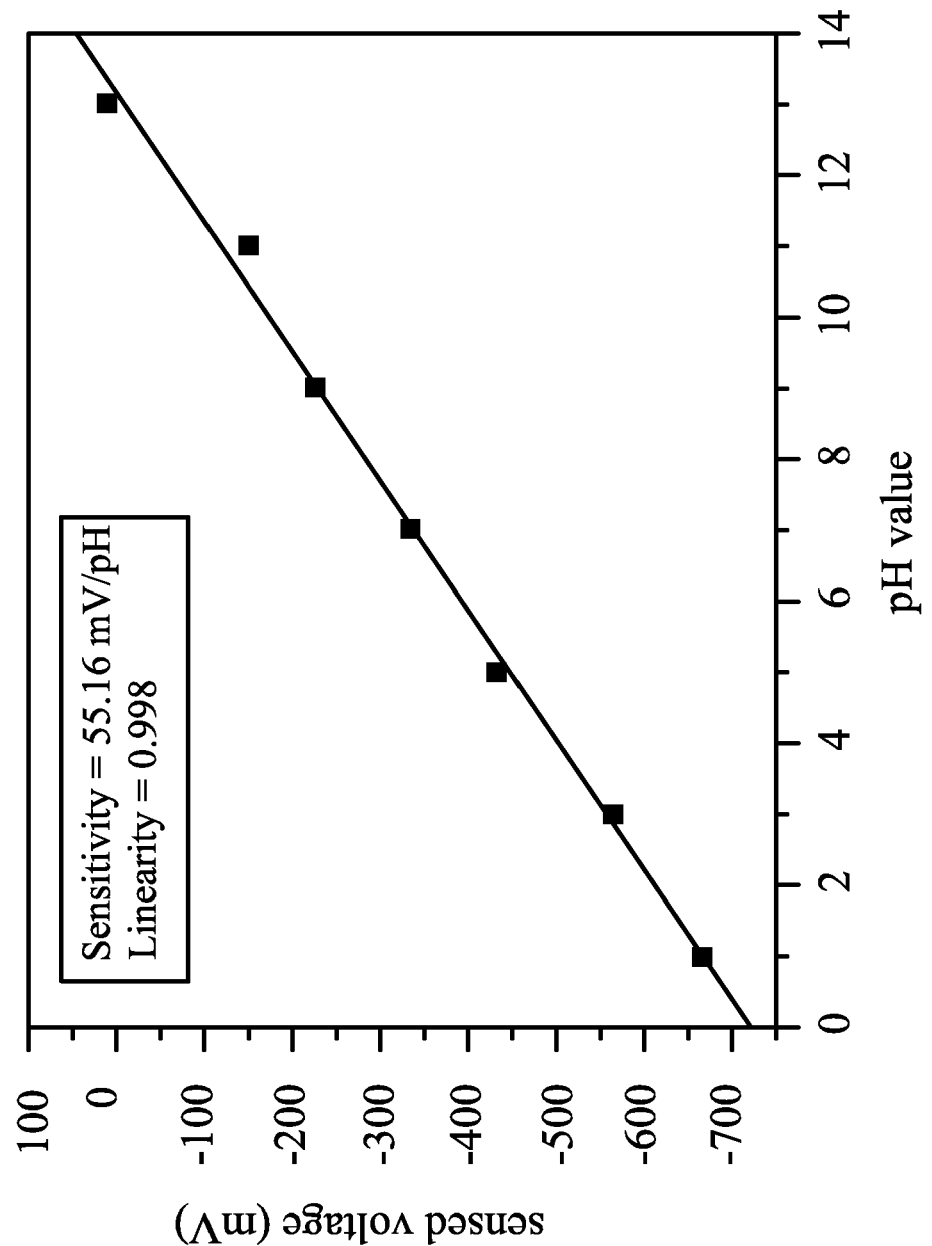
FIG. 4 is a curve diagram representative of sensed voltages of the hydrogen ion concentrations measured from solutions with various acidity according to an embodiment of the present invention.
Figure 5:
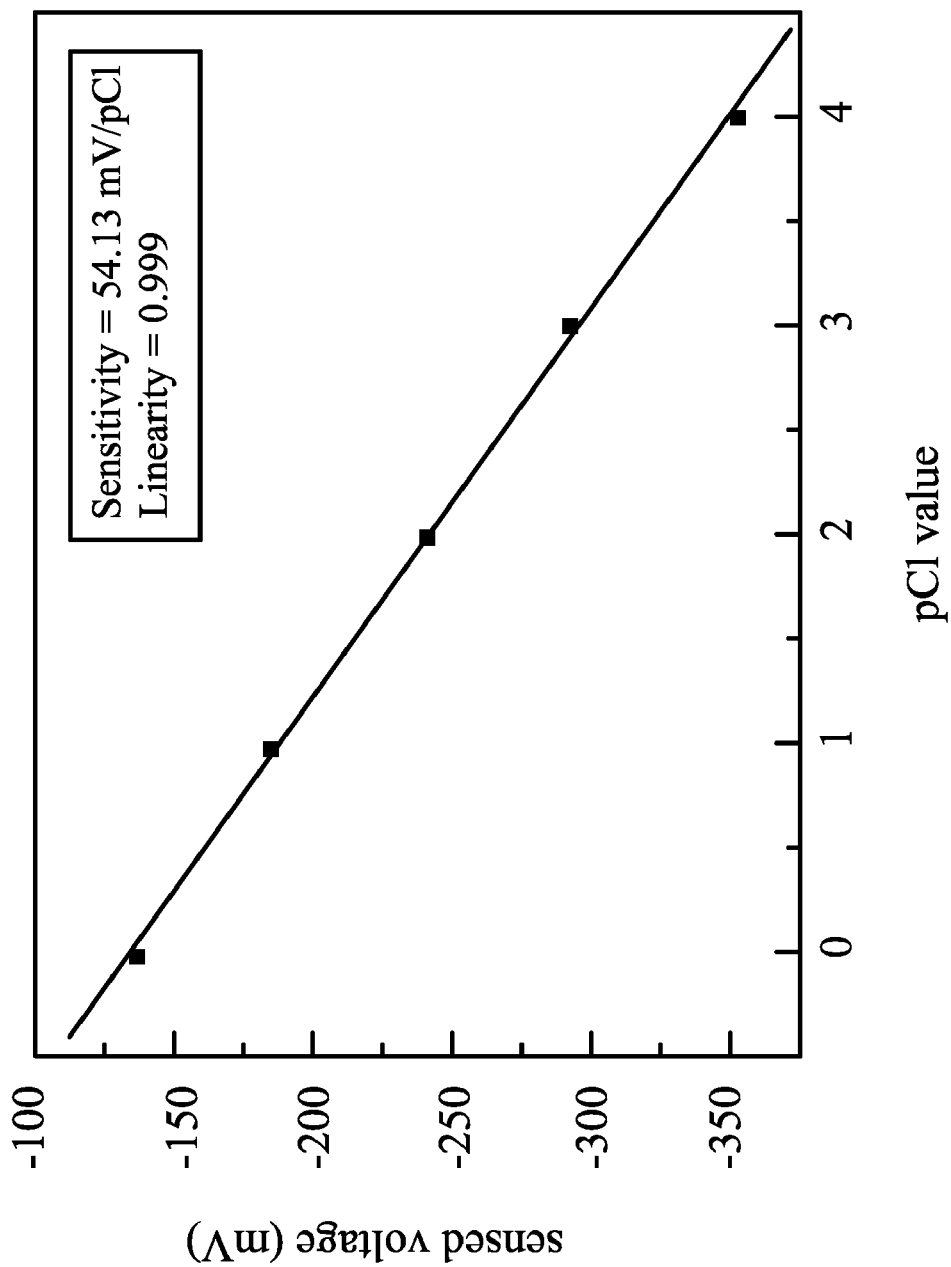
FIG. 5 is a curve diagram representative of sensed voltages of the chlorine ion concentrations measured from solutions with various sodium chloride (NaCl) concentration according to an embodiment of the present invention.

According to the present invention, linear measurement results may be obtained by using the ion concentration measurement system 100. Referring to FIG. 4 and FIG. 5, FIG. 4 is a curve diagram representative of sensed voltages of the hydrogen ion concentrations measured from solutions with various acidity according to an embodiment of the present invention; while FIG. 5 is a curve diagram representative of sensed voltages of the chlorine ion concentrations measured from solutions with various sodium chloride (NaCl) concentration according to an embodiment of the present invention. In FIG. 4, the sensitivities for hydrogen ion concentration measurement are between 50-56 mV/pH (more preferred is 55.16 mV/pH), and the linear regressions are between 0.980-0.999 (more preferred is 0.998); and In FIG. 5, the sensitivities for chlorine ion concentration measurement are between 50-55 mV/pCl (more preferred is 54.13 mV/pCl), and the linear regressions are between 0.980-0.999 (more preferred is 0.999). Thus, the linearity of the sensing signals measured are quite ideal.

By employing the present invention, the ion concentration measurement system 100 may substantially reduce error between sensing signals when measuring hydrogen ion measurement results of sensing signals. The stability of the hydrogen ion sensing results of the sensing signals when the stability thereof was not judged are shown in Table 1, while the stability of the hydrogen ion sensing results of the sensing signals when the stability thereof was judged are shown in Table 2. In the experiment shown in Table 1 and Table 2, the standard solutions of pH1, pH3, pH5, pH7, pH9 and pH11 are respectively measured five times to analyze the accuracy of the measurement system. Table 1 shows that error of the stability of the hydrogen ion sensing results of the sensing signals when the stability thereof was not judged as being between 0.03-0.24, wherein the average error quantity was 0.11; Table 2 shows that error of the stability of the hydrogen ion sensing results of the sensing signals when the stability thereof was judged as being between 0.03-0.08, wherein the average error quantity was 0.06. Thus, the error quantity was under control as the error quantity was reduced from 0.11 to 0.06.

TABLE 1

Measurement results of pH value

| | pH standard solution | | | | | |
|---|---|---|---|---|---|---|
| | 1 | 3 | 5 | 7 | 9 | 11 |
| The first measurement | 0.98 | 2.93 | 5.18 | 7.09 | 9.32 | 11.09 |
| The second measurement | 1.02 | 2.93 | 5.13 | 7.06 | 9.29 | 11.06 |
| The third measurement | 1.03 | 2.95 | 5.17 | 7.06 | 9.18 | 11.12 |
| The fourth measurement | 1.05 | 2.92 | 5.16 | 7.07 | 9.20 | 11.08 |
| The fifth measurement | 1.05 | 2.96 | 5.17 | 7.08 | 9.22 | 11.10 |
| Average | 1.03 | 2.94 | 5.16 | 7.07 | 9.24 | 11.09 |
| Error | 0.03 | 0.06 | 0.16 | 0.07 | 0.24 | 0.09 |
| Average error quantity | | | 0.11 | | | |

TABLE 2

Measurement results of pH value

| | pH standard solution | | | | | |
|---|---|---|---|---|---|---|
| | 1 | 3 | 5 | 7 | 9 | 11 |
| The first measurement | 1.02 | 2.93 | 5.08 | 7.02 | 9.08 | 11.09 |
| The second measurement | 1.01 | 2.95 | 5.10 | 7.06 | 9.10 | 11.05 |
| The third measurement | 1.03 | 2.91 | 5.09 | 7.04 | 9.10 | 11.06 |
| The fourth measurement | 1.05 | 2.98 | 5.04 | 7.06 | 9.04 | 11.04 |
| The fifth measurement | 1.05 | 3.03 | 5.07 | 7.01 | 9.09 | 11.11 |
| Average | 1.03 | 2.96 | 5.08 | 7.04 | 9.08 | 11.07 |
| Error | 0.03 | 0.04 | 0.08 | 0.04 | 0.08 | 0.07 |
| Average error quantity | | | 0.06 | | | |

Accordingly, the stability of chlorine ion measurement results of the sensing signals when the stability thereof is not judged are shown in Table 3, while The stability of chlorine ion measurement results of the sensing signals when the stability thereof is judged are shown in Table 4. In the experiment shown in Table 1 and Table 2, the standard solutions of pCl0, pCl1, pCl2, pCl3 and pCl4 were respectively measured five times to analyze for accuracy of the measurement system. Table 3 shows that error of the stability of chlorine ion measurement results of the sensing signals when the stability thereof was not judged as being between 0.15-0.18, wherein the average error quantity was 0.17; Table 4 shows that error of the stability of chlorine ion measurement results of the sensing signals when the stability thereof was judged as being between 0.03-0.08, wherein the average error quantity was 0.05. Thus, the error quantity was under control as the error quantity was reduced from 0.17 to 0.05.

TABLE 3

Measurement results of pCl value

| | pCl standard solution | | | | |
|---|---|---|---|---|---|
| | 0 | 1 | 2 | 3 | 4 |
| The first measurement | 0.15 | 1.25 | 2.20 | 3.15 | 4.16 |
| The second measurement | 0.09 | 1.18 | 2.18 | 3.19 | 4.21 |
| The third measurement | 0.18 | 1.08 | 2.12 | 3.21 | 4.11 |
| The fourth measurement | 0.17 | 1.13 | 2.21 | 3.16 | 4.19 |
| The fifth measurement | 0.16 | 1.10 | 2.19 | 3.21 | 4.16 |
| Average | 0.15 | 1.15 | 2.18 | 3.18 | 4.17 |
| Respective error | 0.15 | 0.15 | 0.18 | 0.18 | 0.17 |
| Average error quantity | | | 0.17 | | |

TABLE 4

Measurement results of pCl value

| | pCl standard solution | | | | |
|---|---|---|---|---|---|
| | 0 | 1 | 2 | 3 | 4 |
| The first measurement | 0.04 | 0.91 | 1.92 | 3.17 | 4.04 |
| The second measurement | 0.00 | 1.08 | 2.00 | 3.14 | 4.00 |
| The third measurement | 0.08 | 1.08 | 1.95 | 3.02 | 4.08 |
| The fourth measurement | 0.06 | 1.03 | 1.97 | 3.00 | 4.04 |
| The fifth measurement | 0.04 | 1.05 | 1.93 | 3.09 | 4.05 |
| Average | 0.04 | 1.03 | 1.95 | 3.08 | 4.04 |
| Respective error | 0.04 | 0.03 | 0.05 | 0.08 | 0.04 |
| Average error quantity | | | 0.05 | | |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An ion concentration measurement system, comprising:
   at least an end system, comprising:
      a sensing unit configured to measure the ion concentration of a test solution to generate at least a sensing signal;
      a control unit configured to control the acquisition of the sensing signal by determining whether the sensing signal is stable and storing the sensing signal when the sensing signal is determined as stable;
      a display unit configured to display the sensing signal in real time; and
      an end wireless transmission interface configured to transmit the sensing signal wirelessly.

2. The ion concentration measurement system as claimed in claim 1, further comprising:
   a coordinating system, separated from the end system, configured to further process the sensing signal, comprising:
      a coordinating wireless transmission interface configured to receive the sensing signals wirelessly.

3. The ion concentration measurement system as claimed in claim 1, wherein the end system further comprises a serial transmission interface configured to transmit the sensing signal to a computer coupled to the end system.

4. The ion concentration measurement system as claimed in claim 1, further comprises a plurality of end systems configured to respectively measure the ion concentration in different places.

5. The ion concentration measurement system as claimed in claim 1, wherein the control unit is configured to calculate the acidity or basicity of the test solution based on the sensing signal.

6. The ion concentration measurement system as claimed in claim 1, wherein the control unit is configured to store the sensing signal.

7. The ion concentration measurement system as claimed in claim 1, wherein the control unit is configured to calibrate the signal measured by the sensing unit.

8. The ion concentration measurement system as claimed in claim 1, wherein the control unit is configured to determine whether the sensing signal is stable.

9. The ion concentration measurement system as claimed in claim 3, wherein the serial transmission interface is a RS-232 interface.

10. The ion concentration measurement system as claimed in claim 3, wherein the serial transmission interface is an USB interface.

11. The ion concentration measurement system as claimed in claim 1, wherein the display unit is an LCD module.

12. The ion concentration measurement system as claimed in claim 1, wherein the display unit is matrix light emitting diodes.

13. The ion concentration measurement system as claimed in claim 2, wherein the coordinating system further comprises a measurement platform for reading, storing, monitoring, or displaying the sensing signal.

14. The ion concentration measurement system as claimed in claim 1, wherein the control unit further comprises a switch unit configured to turn on or off the end system.

15. The ion concentration measurement system as claimed in claim 13, wherein the ion is hydrogen ion.

16. The ion concentration measurement system as claimed in claim 13, wherein the ion is chlorine ion.

17. An ion concentration measurement method, comprising:
   a measurement procedure, comprising:
      measuring the ion concentration of a test solution to obtain a sensing signal;
      determining whether the sensing signal is stable;
      storing the sensing signal when the sensing signal is determined as stable; and
   a transmission procedure comprises transmitting the sensing signal to an electronic device wirelessly.

18. The ion concentration measurement method as claimed in claim 17, further comprising a calibration procedure, comprising:
   measuring the ion concentration of a plurality of standard solutions to acquire a plurality of calibration signals;
   determining whether the calibration signals are stable; and
   storing the calibration signals when the calibration signals are determined as stable.

19. The ion concentration measurement method as claimed in claim 17, wherein the transmission procedure further comprises transmitting the sensing signal to the electronic device via a serial transmission interface.

20. The ion concentration measurement method as claimed in claim 17, further comprising a route setting procedure comprising allowing an user to set the route through which the sensing signal is stored and accessed.

21. The ion concentration measurement method as claimed in claim 17, further comprising a display procedure comprising displaying the sensing signal in real time during the measurement procedure.

22. The ion concentration measurement method as claimed in claim 17, wherein the ion concentration of the standard solution is between pH1 and pH11.

* * * * *